United States Patent [19]

Saunders

[11] Patent Number: 5,384,239
[45] Date of Patent: Jan. 24, 1995

[54] METHOD FOR ANALYZING THE GLYCATION OF HEMOGLOBIN

[75] Inventor: Alexander Saunders, San Carlos, Calif.

[73] Assignee: Chronomed, Inc., San Carlos, Calif.

[21] Appl. No.: 7,025

[22] Filed: Jan. 21, 1993

Related U.S. Application Data

[63] Continuation of Ser. No. 681,693, Apr. 8, 1991, abandoned.

[51] Int. Cl.$^6$ .......................... A01N 1/02; C12Q 1/00; C12Q 1/54; G01N 33/72
[52] U.S. Cl. ........................................... 435/2; 435/4; 435/14; 436/67
[58] Field of Search .................... 435/4, 14, 2; 436/67

[56] References Cited

U.S. PATENT DOCUMENTS 4,835,097  5/1989  Saunders ................................ 435/4

OTHER PUBLICATIONS

Proceedings, (Published by ISOLAB, INC.) The Role of Glycated Hemoglobin in the Management of Diabetes, Symposium, Sep. 16, 1988, pp. 9–19 and 51–72.

Mortensen, Glycated Hemoglobin, Reaction and Biokinetic Studies Clinical Application of Hemoglobin $A_{1c}$ in the Assessment of Metabolic Control in Children with Diabetes Mellitus, Danish Medical Bulletin 32(6):309–328 (Dec. 1985).

Beach, Kirk W., "A Theoretical Model to Predict the Behavior of Glycosylated Hemoglobin Levels", The Journal of Theoretical Biology, 81:3:547–561, (1979).

Elseweidy, et al., "Changes in glycosylated hemoglobine with red cell aging in normal and diabetic subjects and in newborn infants of normal and diabetic mothers", The Journal of Laboratory and Clinical Medicine, 102:1:628–636, (Jul. 1983).

Bunn, H. F. et al. "The Biosynthesis of Human Hemoglobin $A_{1c}$ Slow Glycosylation of Hemoglobin In Vivo", The Journal of Clinical Investigation, 57:1652–1659 (1976).

Higgins, P. J. et al. "Kinetic Analysis of the Nonenzymatic Glycosylation of Hemoglobin", The Journal of Biological Chemistry, 256(10):5204–5208 (May 25, 1981).

Nakashima, K. et al., Clin. Chem. 35:958–962 (1989).

Primary Examiner—Douglas W. Robinson
Assistant Examiner—S. Saucier
Attorney, Agent, or Firm—Iver P. Cooper

[57] ABSTRACT

As red blood cells age, their hemoglobin is progressively glycosylated. This invention relates to analyzing the history of blood sugar metabolism over a period of several months by taking a blood sample, separating the cells into age-ordered cohorts, determining glycohemoglobin levels in the cells of each cohort, and correlating glycohemoglobin levels with red blood cell age, while correcting for the reversibility of the Amadori rearrangement.

4 Claims, 6 Drawing Sheets

DAYS AGO
SMOOTHED .237

SMOOTHED .217

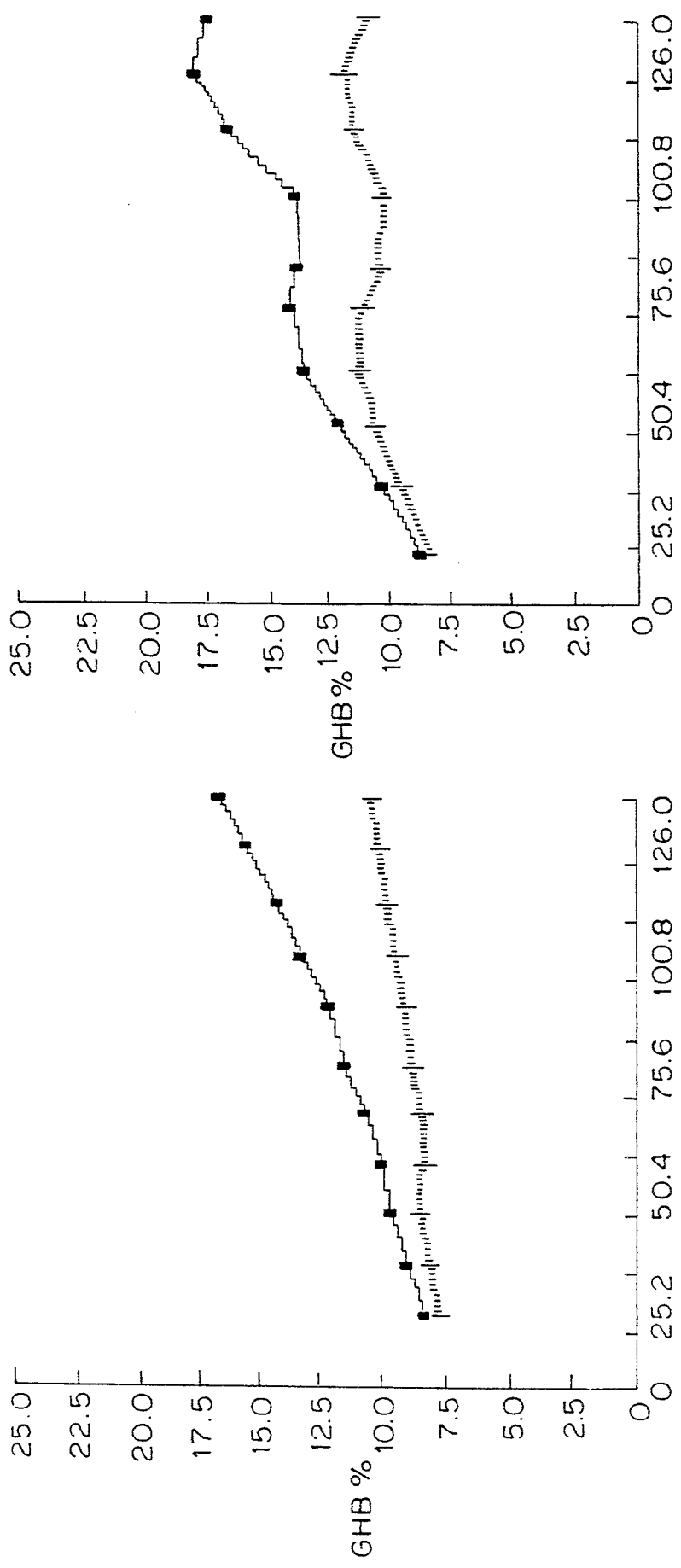

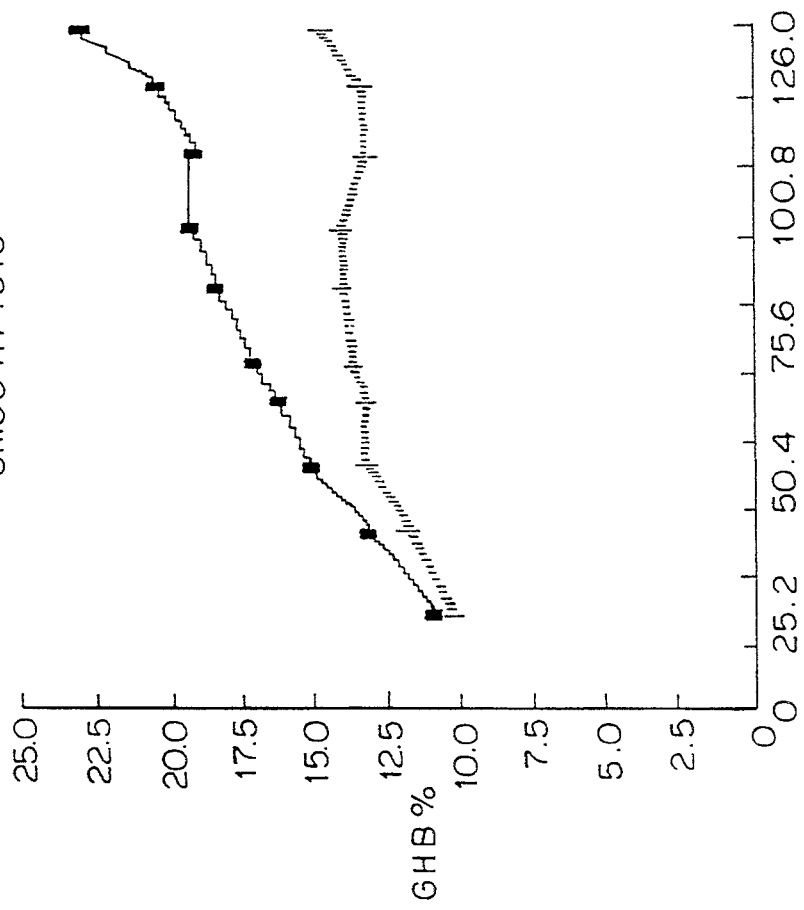
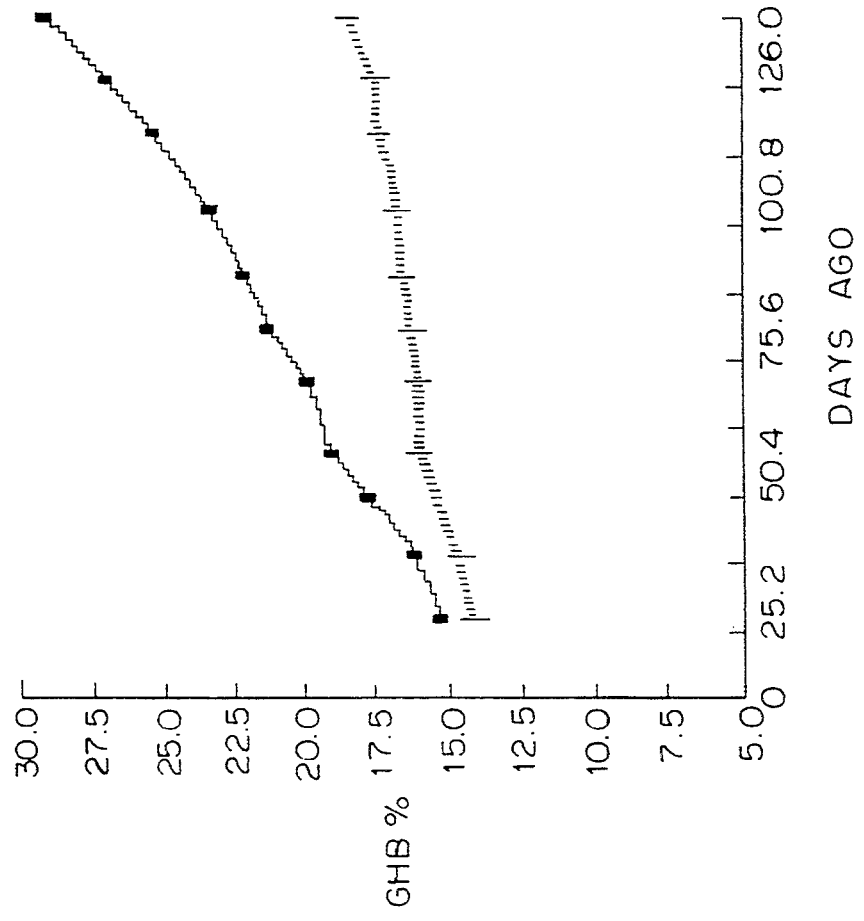

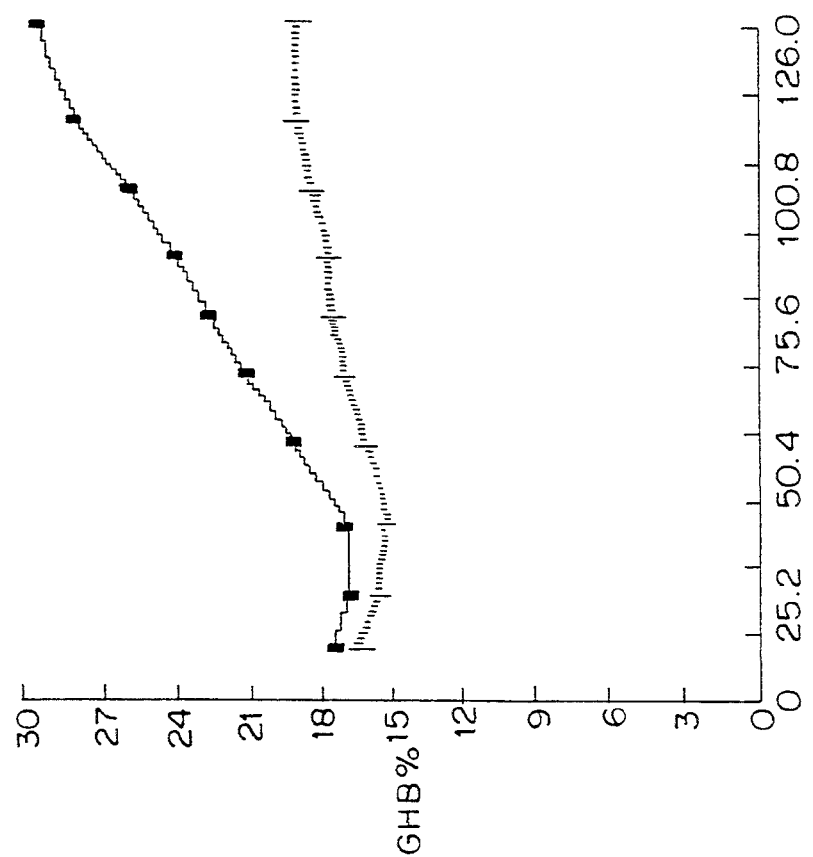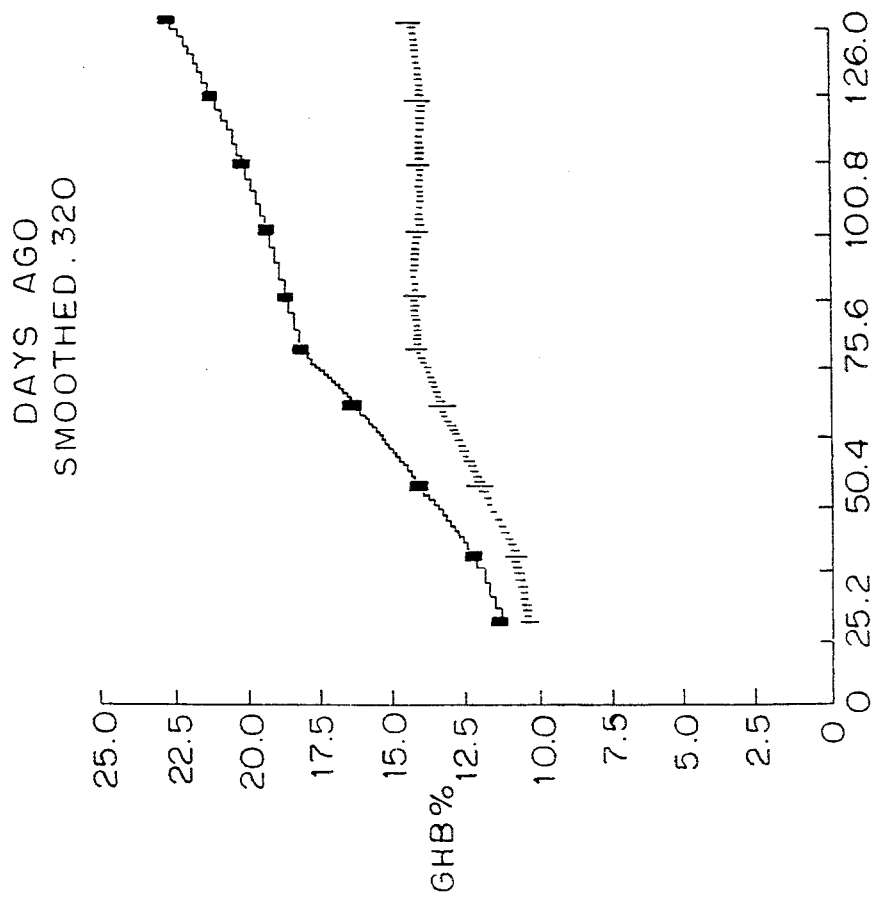

METHOD FOR ANALYZING THE GLYCATION OF HEMOGLOBIN

This application is a continuation of application Ser. No. 07/681,693, filed Apr. 8, 1991, now abandoned.

BACKGROUND OF THE INVENTION

1. Field of the Invention

This invention relates to the analysis of blood sugar metabolism.

2. Information Disclosure Statement

Red blood cells contain hemoglobin, a complex molecule involved in the transport of oxygen and carbon dioxide in the blood. They continuously enter into the circulation from the bone marrow, where they are made. The red blood cells first entering the blood stream are termed reticulocytes, and after the "reticulum" of nucleic acid material is eliminated from the reticulocytes, in the first two days of circulation, the red blood cells continue to circulate, as mature cells, for about 120 days in normal people. After this time the red blood cells are eliminated from circulation and from the body.

The hemoglobin (Hb) molecule consists of heme (a pigment) and globin (a protein). The heme contains iron in the ferrous state. In normal hemoglobin, hemoglobin A (HbA), the protein moiety is formed by two alpha-chain (each 141 amino acids) and two beta chains (each 146 A.A.). Over 100 amino acid sequence variants are known.

It is well known that during their lifetime, red blood cells are bathed in fluid plasma with a continuously changing chemical composition. Some components of the plasma also move freely into and out of the red blood cell through the cell membrane. While in the red blood cell, some of these components exert an influence on the constituent molecules of the red blood cells, particularly on the hemoglobin molecule.

Hemoglobin forms adducts with a variety of molecules, including acetaldehyde, acetate and vitamin B6. Of particular interest in the present instance are the adducts it forms with sugars. These adducts are collectively known as "glycohemoglobins" or "glycated hemoglobins".

The term "glycation" denotes any reaction which links a sugar to a protein. Glycation of a hemoglobin involves the reaction of the carbonyl group of the sugar with a free amine in the hemoglobin. Usually, this free amine is the amino terminal of the beta chain, but it may be the amino terminal of the alpha chain, or a side chain amino group of a lysine residue. The resulting moiety is known as an aldimine. Because there is a hydroxyl group on the carbon adjacent to the carbonyl carbon, a second reaction, the Amadori rearrangement, is possible, which shifts the double bond from C-1 to C-2, forming a ketoamine.

Sugars which form natural adducts with hemoglobin include glucose, 5-deoxy-xylose-1-phosphate, galactose and glucose-6-phosphate. The corresponding keto sugar amines are fructosamine, 5-deoxy-xylulose-1-phosphate, galactulose and fructose-6-phosphate.

When human hemolysate is chromatographed on ion exchange resins, certain negatively charged minor components are eluted before the main HbA peak. In order of elution, these are A1a1, A1a2, A1b, A1c and A1d, and are collectively known as the A1 fraction. These A1 fractions include glycated hemoglobins and possibly other hemoglobin adducts and variants. The A1c fraction includes the glucose and fructosamine adducts of hemoglobin.

Higgins and Bunn (1981) describe the formation of A1c as "nearly irreversible", following their group's earlier report that the Amadori rearrangement is "slightly reversible" (Bunn, et al., 1976). Based on these reports, a person of ordinary skill would disregard "reversibility" as a complicating factor. While, in 1985, Mortenson suggested taking reversibility into account, this is not the current practice. Moreover, Mortenson teaches that there are no age-related differences in HbA1c content among erythrocytes.

The rate of glycation is dependent on blood sugar concentrations. For this reason, glycated hemoglobin measurements have been used to provide an estimate of mean glycemic control over the four to twelve weeks preceding the test. The level of glycated hemoglobin in a red blood cell increases with the age of the red blood cell (and hence the duration of its exposure to blood sugar) and with the mean plasma glucose concentration over the circulating life span of the cell. Traditional glycated hemoglobin measurements cannot detect acute alterations in glycemic status, since such fluctuations will be averaged out as a result of the spread of red blood cell ages in the sample.

Saunders, U.S. Pat. No. 4,835,097 (1989) suggests that the day-to-day control of blood sugar by a diabetic can be determined from a single blood sample by correlating glycohemoglobin levels with blood cell ages on a cell-by-cell basis. While Saunders recognizes that if the reaction is slowly reversible, the history preserved by the oldest blood cells will be lost, he does not describe any means of correcting the data to minimize the distortion of the data by such reversibility.

SUMMARY OF THE INVENTION

It is the object of the present invention to overcome the limitations of conventional glycated hemoglobin measurements as a diagnostic procedure.

The glycated hemoglobin (GHB) test as currently practiced provides information on the average glycemic control of a patient for the past few months. It is a considerable improvement over the use of the blood sugar test in the evaluation of long term glycemic control. Correlation with development of complications of diabetes is fairly good. However, periods of hyperglycemia and of hypoglycemia may be missed when averaged into the single value which represents glycation of hemoglobin in circulating red blood cells whose ages range from 0 to 120 days. The same test performed at higher resolution than a 120 day average could reduce the risk of misinformation. Periods of differing glycemic control could be calendarized for quick review by diabetic care professionals and a more meaningful motivational tool would be available for discussion with patients.

If the process of glycation is irreversible or minimally reversible, as suggested by Bunn et al (1976), then erythrocytes (RBC) of different ages should contain a historical record encoded in their GHb accumulation. A discontinuity in the rate of accumulation would theoretically be represented by a discontinuity in the degree of glycation of RBC plotted in relation to RBC age. A single episode of poor glucose control would first appear as an increase in slope of a Time Resolved Glycated Hemoglobin curve (TRG) related to the most recently produced cells. The resulting discontinuity would propagate through the curve on subsequent samples and eventually disappear in approximately 120 days, as the RBC of that age cohort leave circulation. If as suggested by Mortenson, glycation were freely reversible, there would be no correlation between blood cell age and glycohemoglobin content.

In a preferred embodiment, red blood cells from a single sample are separated according to age into a plurality of age cohorts, e.g., by capillary centrifugation. The age ordering is confirmed, if desired, by measurement of pyruvate kinase levels, or an alternative red blood cell age marker. The average glycated hemoglobin level is determined for the cells of each age cohort.

A transform which adjusts for the reversibility of the Amadori rearrangement is used to linearize the results and thereby facilitate detection of episodic loss of glycemic control. Results in normal volunteers and the majority of patients with glucose intolerance, assumed to be in a steady state, have straight line plots of Time Resolved Glycated hemoglobin (TRG). Discontinuities in a TRG suggest a loss of steady state in glycemic control. A steeper line segment is interpreted as an episode of average higher blood glucose. Presence of both shallow and steep line segments in a TRG would integrate to a time averaged glycated hemoglobin containing compensating errors. The averaged result can be misleading in current practice. Surprisingly, failure to correct for the reversibility of the Amadori rearrangement can also lead to diagnostic errors in an appreciable fraction of cases. As seen in Examples 4 and 5, patients may have the same total glycohemoglobin levels but very different glycemic control histories. Failure to correct for the reversibility of the Amadori rearrangement leads to misinterpretation of the patient's glycemic control, particularly over the oldest events represented in the TRG data.

FIG. 5 illustrates two of the ways in which clinicians may be misled by untransformed TRG plots. In 5(a), the patient is actually in steady state glycemic control. However, the untransformed TRG plot suggests that his or her control is progressively worsening, encouraging a clinical intervention which may be detrimental to the patient. In 5(b), the patient's glycemic control has been improving. However, the untransformed data suggests that his glycemic control is stable. The clinician will likely keep this patient on the same regimen; as a result, the patient's prescribed dose of insulin may become excessive.

BRIEF DESCRIPTION OF THE DRAWINGS

FIG. 2 shows smoothed TRG plots for (a) patient 261 (b) 227. These patients had intermediate total glycohemoglobin levels.

FIG. 3 shows smoothed TRG plots for (a) patient 260, (b) 318, (c) 320 and (d) 306.

DETAILED DESCRIPTION OF THE PREFERRED EMBODIMENT

Figure 1B:
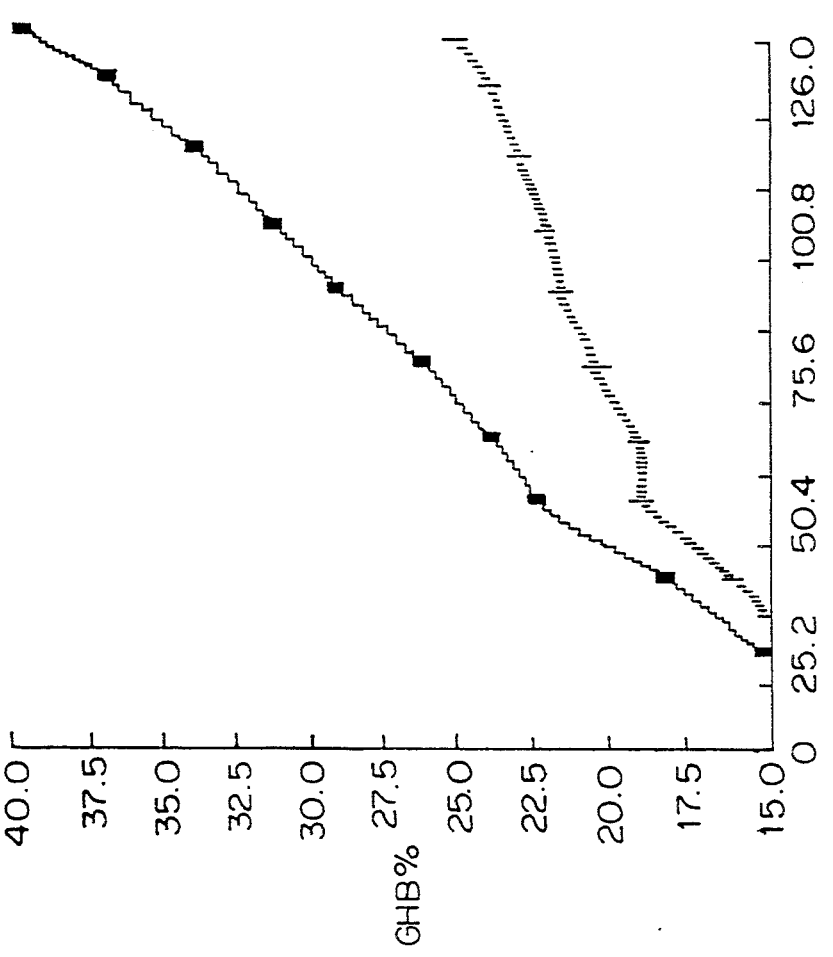
FIG. 1 depicts smoothed, time-resolved glycohemoglobin (TRG) plots for (a) patient 217 and (b) 237, who exhibit steady state glycemic control. The lower trend line is the smoothed, untransformed TRG data; the upper trend line shows the effect of the transform which corrects for reversibility of the Amadori rearrangement.

Red blood samples may be obtained from patients by conventional aseptic techniques. It is then necessary to correlate the age of the red blood cells with their glycated hemoglobin levels, and to correct for the reversibility of the Amadori rearrangement. The true rate of glycation may then be plotted against time for the several months preceding the taking of the sample.

Red blood cells (RBCs) may be fractionated according to age by density gradient methods. RBCs become denser as they age because they shrink, and lose water, without losing solids. Centrifugation, either in a medium of defined density or even in the absence of a foreign medium, causes RBCs to move to an equilibrium position reflective of their density. Physical separation of the red blood cells is not required if cells of different ages can otherwise be distinguished. The resolution and accuracy of the glycation rate analysis is dependent on the number of age cohorts obtained and the distribution of the cells across the cohorts. It is not necessary that glycated hemoglobin levels and red blood cell age be determined on a cell-by-cell basis. Preferably, the number of age cohorts is between about 8 and about 20, with about 10 being especially preferred.

The practitioner may choose to measure, in each age cohort, the overall level of glycated hemoglobins, the level of particular species (e.g., 1a1c), or a combination of the above.

A number of normal hemoglobin adducts and specific abnormal hemoglobins interfere with HbA1c testing. These include the acetate and aldehyde adducts, and hemoglobin F, in which the structure around the terminal valine is different.

Testing for glycated hemoglobin with an affinity method eliminates this set of interferences. All organic compounds having two hydroxyls on adjacent carbon atoms have an affinity for boronate derivatives. By attaching boronate groups to a chromatographic medium, sugar adducts on hemoglobin are separated from non glycated species. It follows, and has been demonstrated, that not all HbA1c is glycated Hb and not all glycated Hb is HbA1c. It also follows, and has been demonstrated, that adducts formed from the various sugar all behave just like the adduct, forming with glucose. Various rare sugars, e.g., rhamnose, xylose, mannose, idose, have been shown to form hemoglobin adducts which behave like more natural sugars in testing situations.

The majority of my testing has been done by affinity chromatography (See Abraham, et al., 1983), which is not sensitive to the aldimine or to non-sugar interferences.

Optionally, the concentration of other chemical species can be measured. For example, the concentration of enzymes (see papers by Seaman, Piomelli and Corash) known to increase or decrease consistently with red blood cell age, e.g., pyruvate kinase, may be used to provide confirmation of the accuracy of the age fractionation.

The correction of the experimental GlyHb levels for the reversibility of the Amadori rearrangement may be carried out with various aids such as nomographs, general purpose computers programmed to carry out the necessary calculations, or dedicated electronics.

EXAMPLE 1

Materials and Methods

Each test requires 0.24 ml of EDTA anticoagulated blood as drawn for routine hematological profiling.

The majority of samples were obtained as remainders after hematologic testing. The screening criterion was a serum glucose level above 11.2 mM. This group of samples was supplemented with a set of random normal controls. Repeat samples were obtained on several patients. After test results were recorded, a single page clinical summary, limited to major diagnosis and information relevant to glucose control and hematology was supplied without reference to patient identity. Such histories were obtained on about ½ of the 72 samples in the study.

Laboratory Tests

Fractionation procedure: A polyethylene pasteur pipette, Scientific Products catalog #P5214-5 was cut short at 9.5 cm and heat sealed at the tip. Special adaptors were prepared to support the capillary portion of the pipette to prevent bending and/or bursting during high speed centrifugation. The bulb of the pipette was cut across squarely and 0.24 ml of anticoagulated blood added with a micropipette. The opening was then covered with a tight fitting plastic cap.

The capillaries were centrifuged at 800× G for 5 minutes, 2900× G for 5 minutes and 14000× G for 10 minutes. This last centrifugation was done in a microhematocrit centrifuge with a modified rotor. The bulb and the part of the capillary stem of the pipette which contained only plasma, were cut away before this final centrifugation. The adaptor is a thin walled aluminum tube, sealed at one end with metal filled epoxy, so that that whole tube may be filled with water. Preliminary studies had shown that the first two centrifugation speed were insufficient, and extending the last beyond 10 minutes did not improve resolution. However the initial centrifugation is necessary to drive all cells into the capillary. After the last centrifugation, the column of red blood cells in the capillary was cut into 10 equal fragments, using an animal claw clipper which has a guillotine action. As they were cut, each fragment of polyethylene tube fell directly into a test tube containing 1 ml of phosphate buffered saline (PBS). Cells were suspended in the BPS by vortexing.

A 20 microliter aliquot of each fraction was diluted in 1 ml of deionized water containing 0.01% of Triton×100 (Sigma) and the total hemoglobin was measured at 414 nm in a Beckman DB spectrophotometer. Each saline suspended fraction volume was then adjusted to a constant concentration of hemoglobin (Hb) with PBS. An aliquot of whole blood was similarly diluted with PBS. Two assays were performed on each fraction and whole blood aliquot.

Glycated Hemoglobin: The Glycogel B procedure (Pierce, Rockford Ill.) was performed exactly according to manufacturer's instructions. This is a minicolumn procedure based on affinity chromatography (Abraham, et al., 1983). The test has been cleared by FDA for "in vitro diagnostic use". The columns were regenerated, also according to manufacturer's recommendations, but no column was used more than once per day.

Pyruvate Kinase Activity: The assay used the reagents of Seaman, et al. (1980), but the assay was modified to account for the spectral overlap of hemoglobin and NADH at 340–350 nm and for the loss of NADH absorption during incubation in the absence of cells. Results are expressed as NADH utilization per minute, adjusted for hemoglobin concentration, and multiplied by a constant so as to fit on the same graph as the TRG results. Since the main purpose of PK assay was to confirm the time ordering of fractions, the relative scale was considered sufficient.

Mathematical Analysis

RBC age of fractions was estimated from the hemoglobin measurements of each fraction. First the optical density (O.D.) of all fractions were summed. Then the O.D. of each fraction was normalized to represent a proportion of an assumed 126 day life span, which includes bone marrow residence of cells containing Hb. The midpoint of each fraction was taken as the average age of cells in that fraction, accumulating from fraction 1 towards the highest fractions.

The pyruvate kinase (PK) activity was subjected to regression and correlation analysis against fraction number, to determine if the sample had significant PK activity and if a linear fit was acceptable. If the correlation coefficient was better than $-0.85$, the fractionation procedure was considered to be linear. Fraction 1 was excluded from this analysis because it contains white blood cells and reticulocytes, both of which have high PK activity.

Equations set forth below were used as a basis of models for curve fitting TRG in a spread sheet computer program on 3 normal and 3 severely abnormal samples with the aim of linearizing the results.

A first degree of smoothing of the data by averaging adjacent fraction results was applied to the data after the linearizing transform. This smoothing was considered necessary because of limitations in overall precision of the method with available equipment.

The spread sheet employed for all the above analyses is IAC Calc, Artsci, North Hollywood, Calif. It is similar to, but not identical to Visicalc, for the Apple II computers. This program facilitated the rapid recalculations used in deriving the final equation and provided a template for all necessary calculations.

Reproducibility Study

Reproducibility of the minicolumn affinity chromatography method was tested on hemolysates at the level of 3.5, 10 and 16% GHb. Five replicates were performed from each hemolysate, with each of three types of columns: previously unused columns (designated "fresh"), columns previously used 20+/-3 times and regenerated according to manufacturer's recommendations, and columns previously used and regenerated five times, but left at room temperature overnight on several occasions.

Reproducibility of the overall method, including capillary centrifugation, fractionation procedure, and transformation was also tested. The goal of this test was to demonstrate reproducibility of a moderate discontinuity in a sample, without randomly introducing other significant discontinuities. For this purpose, a patient sample with an integrated GHb of about 7% was put through the whole procedure six times, using six separate capillary pipettes with six aliquots of 240 microliters of whole blood. Hemolysates from each of 60 fractions (10 fractions from each of the six fractionations)

was analyzed, using frequently used and fresh affinity minicolumns. The two results from each hemolysate were averaged, to reduce variability due to minicolumn analysis and the results were plotted in the standard format, expanding the graph both in time and GHb dimension, so that differences in replicates, plotted on one graph, would stand out.

The single results from well used and fresh columns were also compared in this experiment. In addition, the six centrifugations were actually performed as three pairs of capillaries on the microhematocrit centrifuge. Within centrifugation and between centrifugation reproducibility was examined.

In order to provide a numerical means of comparison, the longer linear portion of this data, representing the oldest 8 fractions, were analyzed by regression analysis, the slope of each plot being of most interest. These are compared to the same statistics in the shorter linear segment. It is recognized that this analysis is not a conventional approach, but it is used here to evaluate the observed imprecisions of analysis.

As a result of the reproducibility study, each set of results was examined on the day it was chemically analyzed. Fractions which were gross outliers on minicolumn analysis were re-run. If they persisted as outliers, they were accepted as such in the data set.

Test Set

After the linearizing algorithm was devised on a "practice set" of samples as described above, the procedure was repeated on a large number of EDTA anticoagulated samples. The results were plotted as transformed GHb % vs RBC age (Days Ago). These plots were then examined for significant curvature and for significant discontinuities. This "test set" was totally independent of the practice set used for method design.

Results

The PK assay was developed while the first 20 samples were run for TRG. Of the 52 samples on which PK assays were available, only two were found not to have a correlation coefficient better than $-0.85$. The actual range of correlation coefficients was $-0.75$ to $-0.99$. The two deviants were traced to a variation in enzymatic activity which depended on the amount of red cell suspension used in the assay. When the initial cell suspensions are diluted to constant concentration, this deviation was no longer observed.

Because the PK assay indicated that the fractionation technique is acceptable, all the 72 samples in the study were pooled for further analysis.

By applying the linearizing algorithm to GHb results in fractions, control (normal) samples did become linear, within measurement limits. After developing a good fit on these preliminary samples, the whole data set was subjected to a standard transform. The equation used was:

$$y' = y \frac{1 - 0.009}{e \wedge (-KT(10/c))}$$

where
y represents raw data of each fraction
y' transformed data of the same fraction
K rate of the reverse reaction
e the base of the natural logarithm
T time, as calculated from Hb of fractions
10/c a correction required when the number of fractions is not 10
c the number of fractions
∧ exponentiation operator
$-0.009$ an offset to adjust the value of first fraction As can be seen, the denominator of this equation resembles the standard equation for exponential decay. In this application, the chemical reaction starting with the aldimine (Schiff base) and having the ketoamine GHb as product is considered to be reversible. The forward reaction results in the accumulation of glycated products (GHb). The forward reaction has its own constant (see Bunn, et al., 1976; Mortenson, 1985), but has a variable rate, according to concentration of aldimine which in turn is in a faster equilibrium state dependent on plasma glucose concentration. The reverse reaction constant, K in the above equation, was derived as suggested by Bunn by an interactive process. For the minicolumn method used for the present data base, $K=0.45$ days$^{-1}$. It is important to recognize that K is strongly dependent on the method of chemical analysis. For example, preliminary data suggest that after incubating RBC in pH 5.2 isotonic solution (see Mullins, et al., 1986), $K=0.09$ for the same minicolumns. This is closer to the 1% per day decay previously suggested for HbA1c as determined by ion exchange chromatography (Bunn, et al. 1983). The offset ($-0.009$) is used to equate the transformed to the untransformed first fraction. Another value could be used to adjust the mean of transformed to the mean of untransformed data. Use of this constant does not change the patterns in the data.

Preferably, the transformed data is also smoothed, e.g., according to the formula $$Y_{s,i} = (Y_{n,i} + Y_{n,i-1})/2$$

where $i=2$ to n, n is the total number of data points, $Y_{n,i}$ is the ith unsmoothed data point and $Y_{s,i}$ is the ith smoothed data point.

Reproducibility

An occasional gross outlier was observed in the data when using columns which had been stored for more than a few months at 0-4 degrees Centigrade. Both fresh and regenerated columns could result in outliers and it is suspected that air bubbles hidden within the gel may be the cause. Once a column produces outlying low results, it will continue to do so on subsequent use. However, back-flushing such a column often works as a corrective measure. When gross outliers were encountered, a second measurement was made of the involved and adjacent fractions to verify or replace the original results.

Initially all discontinuities were treated as outliers. It soon became apparent that discontinuities were not procedurally related artifacts, but truly represented content of the fraction.

Minicolumn reproducibility is summarized in Table 1. It may be noted that even after many regenerations, the columns give very similar values to fresh columns, and have similar coefficients of variation (C.V.).

Table 2 contains a summary of the statistical analyses of six replicate fractionations. It should be noted that, although the slope of the first 3 fractions is fairly constant, the slope of the last 8 fractions is variable. Note that in each set, there is a considerable difference in slope between the first three and the last eight fractions.

All six sets found the position of the discontinuity at fraction 3, equivalent to about 50 days ago.

Provided that samples yielding gross outliers are remeasured, it is concluded that within-run reproducibility is satisfactory for the detection and grading of discontinuities in clinical samples.

Table 3 contains a summary characterizing TRG curves of a series of individual samples. Discontinuities ranging from + to + + + represent increasing severity in deviation from a single straight line. Only 2 samples out of 72 in this study show continuous curvature. One was from a patient with a complex endocrine disorder including diabetes mellitus. The other was from a patient with very recent onset diabetes. The 70 other samples have either a single straight line pattern or a series of straight lines of different slope, connected at fairly sharp vertices. These straight line segments, whatever their length, are interpreted as periods of steady state in glucose control. A change in slope represents a change in glucose control. A steeper slope is interpreted as a period of higher average plasma glucose. This interpretation is supported by histories of patients without TRG discontinuities in which strong correlation exists between slope of GHb accumulation and repeated plasma glucose determination. For example, the steepest slope found to date is from a patient repeatedly hospitalized for various manifestations of hyperglycemia and keto acidosis and blood sugars ranging up to 44 mM.

ate the glycemic control exercised by the patient over the preceding months.

Materials and Methods

Samples for the study were EDTA anticoagulated blood as usually drawn for hematology profiling and were identified by having a serum glucose value greater than 11.2 mM. A group of non diabetic individuals were similarly identified and had an average blood glucose of 5.5 mM. The screening process was supplemented with a number of samples. A set of samples were obtained from a patient group recently admitted to a specialty endocrine practice. In this last group, there was increased expectation of changed glucose control in the last 4-6 weeks.

There were 8 normal controls, and 98 patients. However patients found to have recent blood transfusion were excluded from the analysis. In some patients with dialysis, the results were not interpretable, and these were also excluded from final analysis. There were a total of 101 usable samples in the data base. Men and women were about equally distributed. The age range was from 2 to 92 years. Patients with pharmacologically induced glucose intolerance as well as IDDM and NIDDM patients were included in the study. There was no attempt at random sampling. Rather the intention was to obtain a large variety of different patterns, without any prior knowledge of frequency of occurrence. Five patients are represented more than once in the study, in order to determine if patterns are unique to individuals or to historical events. One patient was followed at monthly intervals for 9 months.

The complete analytical methods are described in Example 1. Briefly a whole blood aliquot was analyzed in parallel with ten aliquots obtained by a simple density fractionation method. Thereafter each aliquot was treated identically in analysis for pyruvate kinase (PK) and for glycated hemoglobin (GHb) by standard methods. Red blood cell age was estimated photometrically by relating total Hb of single fractions to the sum total Hb of all fractions, assuming that the lightest cells were the youngest and that the cells were in approximate density order. RBC age was translated to "days ago" for presentation. The results for GHb determinations were next transformed by an algorithm which adjusts for the slowly reversible kinetics of GHb accumulation.

A variety of graphical presentations of the patient data were devised, and evaluated informally by physicians, nurses, technologists and patients. There was no consensus on an optimal display. The display used herein is a plot of GHb accumulation in RBC of different ages, based on the assumption that all RBC continuously convert Hb to GHb at a rate determined by plasma glucose concentration.

To evaluate and summarize the results, the data was tabulated according to a two way classification scheme. One dimension represents information available from current practice, i.e. the integrated GHb representing the average of 120 days of glucose control with three

TABLE 1

| | Reproducibility of Minicolumns | | | | | | | | |
|---|---|---|---|---|---|---|---|---|---|
| | New Columns | | | 5 Times Regenerated | | | 20+ Times Regenerated | | |
| | Mean | +/− SD | CV% | Mean | +/− SD | CV% | Meam | +/− SD | CV% |
| High | 18.4 | .59 | 3.25 | 19.1 | 1.15 | 6.0 | 19.04 | .71 | 3.72 |
| Medium | 10.66 | .23 | 2.3 | 10.54 | .58 | 5.5 | 10.64 | .25 | 2.4 |
| Low | 4.42 | .35 | 6.1 | N/A | N/A | N/A | 4.07 | .41 | 10.2 |

TABLE 2

Regression and Correlations Statistics For Six Replicate Fractionations (A-F) of the Same Blood Sample

| | A | B | C | D | E | F | Pool |
|---|---|---|---|---|---|---|---|
| Mean GHb of First 3 Fractions Of Indicated Fractionation | | | | | | | |
| mean | 6.42 | 5.71 | 5.88 | 5.64 | 6.09 | 6.15 | 5.95 |
| SD | 1.79 | 1.42 | 1.70 | 1.59 | 1.74 | 1.37 | 1.37 |
| r | 0.993 | 0.988 | 0.989 | 0.979 | 0.992 | 0.988 | 0.977 |
| int | 2.43 | 2.82 | 2.33 | 2.90 | 2.91 | 3.67 | 2.87 |
| slope | 0.140 | 0.134 | 1.40 | 0.124 | 0.133 | 0.100 | 0.129 |
| Mean GHb of Last 8 Fractions of Indicated Fractionation | | | | | | | |
| mean | 11.59 | 10.56 | 10.73 | 10.66 | 10.82 | 11.08 | 10.91 |
| SD | 2.1 | 2.27 | 1.84 | 2.02 | 2.04 | 2.05 | 1.97 |
| r | 0.994 | 0.998 | 0.994 | 0.985 | 0.997 | 0.987 | 0.983 |
| int | 5.53 | 5.10 | 5.69 | 5.64 | 5.37 | 5.34 | 5.44 |
| slope | 0.074 | 0.073 | 0.061 | 0.065 | 0.069 | 0.070 | 0.069 |

Independent variable is Days Ago
Dependent variable is the Transformed GHb
r: coefficient of correlation

TABLE 3

Summary of the Appearance of TRG Curves

| Curve Shape | Linear | Discontinuous | | | Curved |
|---|---|---|---|---|---|
| | | + | ++ | +++ | |
| Number Observed | 34 | 11 | 12 | 13 | 2 |

EXAMPLE 2

This example relates to a clinical study in which information from a single blood sample was used to evalulevels: normal, up to 8%; intermediate, 8% to 12%; and high, above 12%. An arbitrary scale was developed for the other dimension, using the shape of the Time Resolved Glycohemoglobin graphic for each sample individually. The graphic was either linear, or curved, or contained discontinuities at one of three levels of severity: + discontinuities represent subtle distortions of a straight line which are probably meaningful only in light of other available history, ++ and +++ are obvious deviations from a straight line that would require further investigation and explanation when encountered in practice.

Patients' histories, when available, were summarized on a standard form. A total of 62 histories were obtained. In some instances, there was only a brief relevant comment by a physician over the telephone. Any known cause for a change on glycemic control was compared to the discontinuities in TRG graphs. For purpose of communicating the relationship of history to graphs, a set of very abbreviated excerpts of these histories is given in the results.

Results

Pyruvate kinase (PK) activity of the top fraction was consistently much higher than the activity of any other fraction. There had been no attempt to separate white cells from this fraction and it was concluded that the elevation was due to WBC contamination. Microscopic examination of several samples confirmed that WBC were limited to the top fraction.

Initially PK was used as a means of optimizing the density separation method in terms of centrifuge speed and time of centrifugation. After this optimization, correlation within sample ranged from −0.75 to −0.99 and was better than −0.85 in 90% of samples.

The PK data was also plotted along with the TRG results to search out commonality of discontinuities. Except in the instance of severe blood loss, there was no such commonality. Discontinuities in PK curves tended to be single point outliers which were attributed to analytical imprecision. In summary, the PK test did serve its purpose of confirming the age separation of RBC by their density and by supplying a cross reference to the work of others. PK analysis was discontinued after about 90 samples.

The Examples which follow draw upon TRG patterns seen in this study.

SUMMARY OF DATA BASE

In Table 4, the database has been classified in one dimension by the overall GHb level, used as a marker in current practice, into normal, intermediate and abnormal. The other dimension highlights the additional information available from time resolution of GHb. It should be emphasized that this is not selected data but a summary of all data obtained during the course of the study. However there was no attempt at formal randomization during the acquisition process. Therefore the incidence of each type of result can not be determined from the table.

The difference between discontinuities and curves is a matter of degree. Results tabulated as curved show a gradual change from one slope to another. Discontinuities tend to change more suddenly in time, and therefore to show two or more distinctive slopes. Samples with more frequent irregularities are classified under discontinuities. The eighteen samples in which the integrated whole blood GHb is normal but TRG has significant information should be noted especially.

TABLE 4

| TIME RESOLVED VS BLOOD GLYCOHEMOGLOBIN TIME RESOLVED GRAPHIC | | | | | |
|---|---|---|---|---|---|
| Whole Blood Result | Shape | | | | |
| | Linear | Discontinuous | | | Totals |
| | | + | ++ | +++ | Curved | |
| Normal | 18 | 9 | 13 | 3 | 2 | 45 |
| Intermediate | 6 | 6 | 12 | 5 | - | 29 |
| Abnormal | 8 | 3 | 9 | 4 | 3 | 27 |
| Totals | 32 | 18 | 35 | 12 | 5 | 101 |

Discontinuities exist in the accumulation rate of glycosylated product. These discontinuities relate to a variety of historical episodes which can account for changes in average metabolic control of glucose. Only prolonged episodes can be resolved at this stage of development of the methods because shorter periods may be averaged into a straight line. The actual resolution in this study is probably about 14 days. With introduction of automation and use of more fractions, the resolution and the precision are expected to improve, but may be expected to have some biologically based limitations.

Episodes relating to discontinuities in TRG include changes in diet, medication, and exercise. Episodes of emotional stress and infection, such as pyelonephritis were also related, but tend to be represented by a more gradual change in accumulation of GHb. For example, a patient beginning detailed plans for her wedding showed a gradually steepening curve, in spite of making no concurrent changes in medication, diet, or exercise.

Onset of diabetes was observed in several patients in the study. In one patient, the date of onset was known to within several weeks because a preschool physical examination, including laboratory results, was normal in August, and symptoms first appeared in mid September with laboratory confirmation before the end of the month. The TRG of this patient in December is consistent with a gradually increasing blood glucose level over the period studied. Two months after the first sample, the TRG of this patient was linear, with the same steep slope that had been observed in the most recent portion of the first sample. In another patient, diabetes was diagnosed at his return from a two month trip to the Orient. The TRG was linear and steep at the time of diagnosis, suggesting that the condition had been present for more than a complete cycle of RBC replacement of 4 months. In this instance the absence of a discontinuity in the TRG may also provide information which is not otherwise available.

In at least 4 patients, an extended flat portion of the TRG curve was correlated with episodes of hypoglycemia. One example (FIG. 2(b)) is a 66 year old male NIDDM patient, taking insulin, who frequently foregoes breakfast and often forgets lunch until he becomes lightheaded.

The two way classification of the data base in Table 4 addresses the issue of information content of TRG exceeding the information content of GHb done on a whole blood hemolysate. With some exceptions, not dealt with in the table, a linear TRG (one without discontinuities) is assumed to have the same information content as a single GHb. Discontinuities are further qualified as +, ++, or +++ as an arbitrary scaling of severity. Although examples may be given of significant information in a + sample, a conservative approach is to count only ++ and +++ as significantly exceeding information content of current practice.

The estimated incidence of added value indicated in Table 4 may be low for two reasons. First, for the date of onset of diabetes a TRG may provide significant information even if it is completely linear. Second, a completely linear TRG, noted 4-6 weeks after an attempted change in therapy, strongly suggests that the change did not have the desired result. Examining GHb alone would not segregate these patients successfully for further investigation. Repeated fructosamine testing may be successful in identifying these patients. However interpretation of this test is strongly influenced by the turnover rate of plasma proteins which is far less consistent than RBC turnover and would require repeated testing as well as a baseline value.

The true incidence of added value of TRG in a variety of institutional or practice situations will not be known until a randomized study is undertaken in each setting. The present study, which was not formally randomized, can only suggest that the incidence of added value is conservatively 30%. Such added value is observed as often in patients with normal whole blood hemolysate GHb as in patients with slight or even severe abnormality by current testing practice. Therefore the whole blood GHb result is not likely to act as a screening test for TRG.

Table 4 does not analyze separately the added value attributable to correction for reversibility of the Amadori rearrangement. This point will be developed in the Examples which follow.

EXAMPLE 3

This Example shows how average blood glucose levels are related to the slope of the time-resolved glycohemoglobin curves when patients are in "steady state" vis-a-vis glycemic control.

Figure 1A:
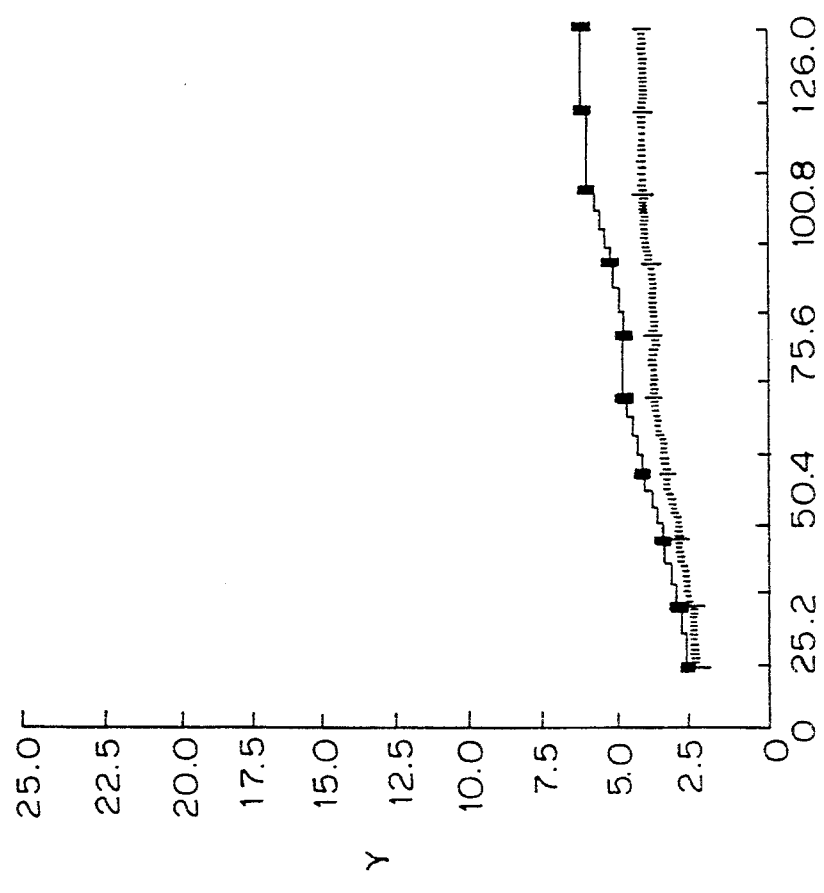

At one extreme, we have patient 217 (FIG. 1(a)). This was a 74 year old white male with a blood glucose level of 11.4 mM at the time the sample was taken. the sample had a total glycohemoglobin level of 3.5% (relative to total hemoglobin). This patient was not diabetic. He was admitted to the hospital with acute bleeding pyloric channel ulcer and was put on intravenous glucose infusion before the blood sample was taken.

At the other extreme, we have patient 237 (FIG. 1(b)) a 19 year old white male suffering from Type I diabetes for the last ten years. He was under severe stress for at least the last two months and had four previous hospital admissions for hyperglycomia, ketoacidosis and severe nosebleed. He was admitted with a blood sugar level of 44.2 mM; the total GHb in his sample was 21.7%, It will be noted that the slope of the TRG plot for patient 217 is substantially less than that for patient 237. Thus, the steeper the slope, the higher the blood glucose level.

The point is further illustrated by patient 261 (FIG. 2(a)), whose TRG curve has a moderate slope. This was a 71 year old white woman admitted for chemotherapy (for breast cancer), with blood sugar levels ranging from 11.9 to 26 mM. Her sample GHb level was 9%. She thus represents an intermediate case.

FIGS. 1(a), 1(b) and 2(a) present both transformed and untransformed TRG plots. Failure to correct for the reversibility of the Amadori rearrangement decreases the apparent steepness of the TRG plot.

EXAMPLE 4

This example illustrates how patients with GHb levels in the range of 8-12% can exhibit very different TRG curves, and that the discontinuities in the TRG curves correlate with patient histories.

As mentioned in the previous example, patient 261, with a GHb level of 9% exhibited steady-state glycemic control, as indicated by a straight line TRG plot. (FIG. 2(a)).

Patient 227 (FIG. 2(b)) presents a more complex picture. He is a 66 year old white male with Type II diabetes, diagnosed four years previously. He is physically very active and often forgets breakfast and even lunch. His total GHb level was 10.8%. His TRG curve reveals hypoglycemic episodes (horizontal lines) interspersed with periods of steady state glycemic control typical of diabetics (moderately sloped lines). Hypoglycemia, i.e., excessively low blood sugar, in this patient was due to the insulin dosage not matching his life style. When the physician corrected the insulin dosage approximately 60 "days ago" a more stable result followed. Without correction for the reversibility of the Amadori rearrangement, the rises and falls in his TRG curve appear less pronounced, therefore suggesting to the clinician that patient 227's glycemic control was more stable than it was in fact.

Interpretation of a horizontal TRG segment as a hypoglycemic episode is valid only if the normal accumulation of GHb produces a TRG with a constant upward slope.

EXAMPLE 5

This example illustrates the utility of TRG analysis with patients exhibiting high glycohemoglobin levels. Patient 260 (FIG. 3(a)) evidences steady state glycemic control. The total HGb level in his sample was 18.3%.

Patient 306 (FIG. 3(b)) is a middle aged hispanic male whose treatment for diabetes began four weeks ago. The older section of the TRG has a slope typical for a diabetic. The most recent section is also horizontal, consistent with the patient's favorable response to insulin therapy. His total GHb was 16.6%.

Patient 320 (FIG. 3(c)) is a 26 month old white male with Type I diabetes for 8 months before the sample was taken. His TRG reveals recent deterioration in glycemic control due to chronic ear infection.

Patient 318 (FIG. 3(b)) is an eight year old white female with Type I diabetes mellitus for more than one year. The parents are both medical professionals and monitor the child closely. The sample's total GlyHb was 13.5%. However, the period from 100-110 days before sampling was a documented period of hypoglycemia (blood glucose 2.6-4.1 mM) which correlates with an almost horizontal section of the transformed TRG curve. Except for the hypoglycemic episode, the rate of GHb accumulation is one usually associated with a whole blood GHb of about 16%. Although some distortion from steady-state is apparent without the transform, failure to correct makes it more difficult to correlate the TRG curve with the patient history. In the untransformed data, there appears to be a long hypoglycemic period running from about 50 days prior to sampling to at least 100 days before. In the transformed data, it is apparent that the hypoglycemic period was shorter and older, running from 100-110 days before sampling. Moreover, the failure to transform the data masks the period of high blood sugar levels apparently preceding this hypoglycemic episode.

EXAMPLE 6

Figure 4A:
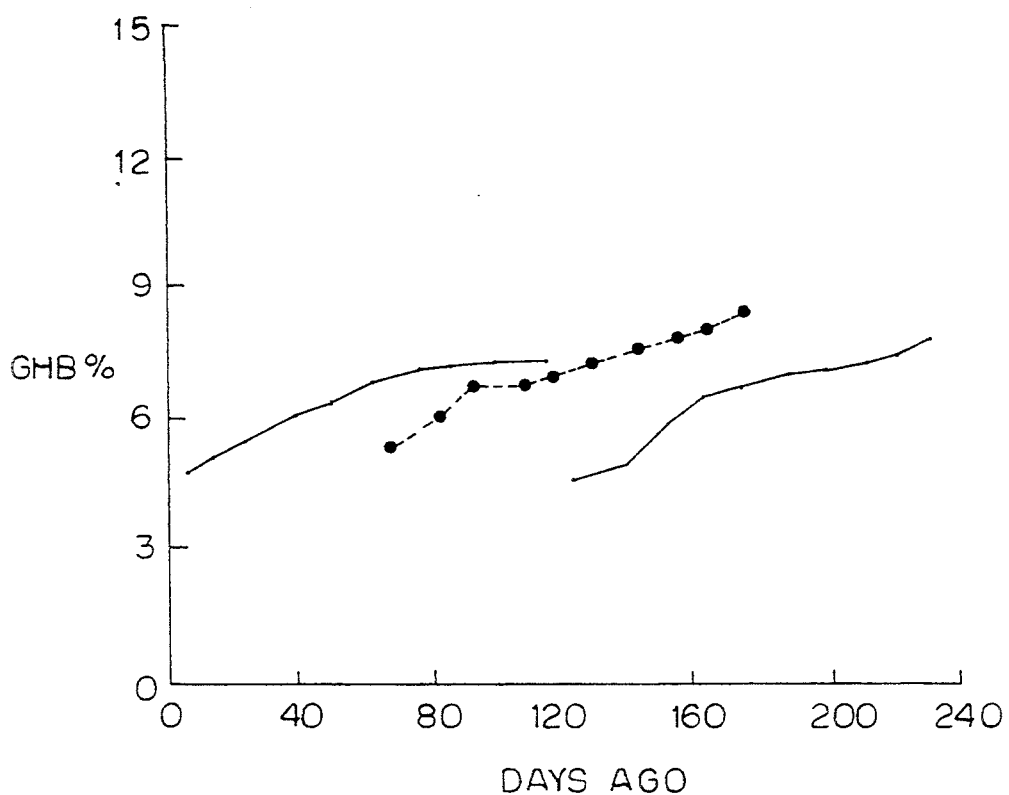
FIG. 4(a) shows the untransformed data; 4(b) illustrates the effect of the correction.
Figure 4B:
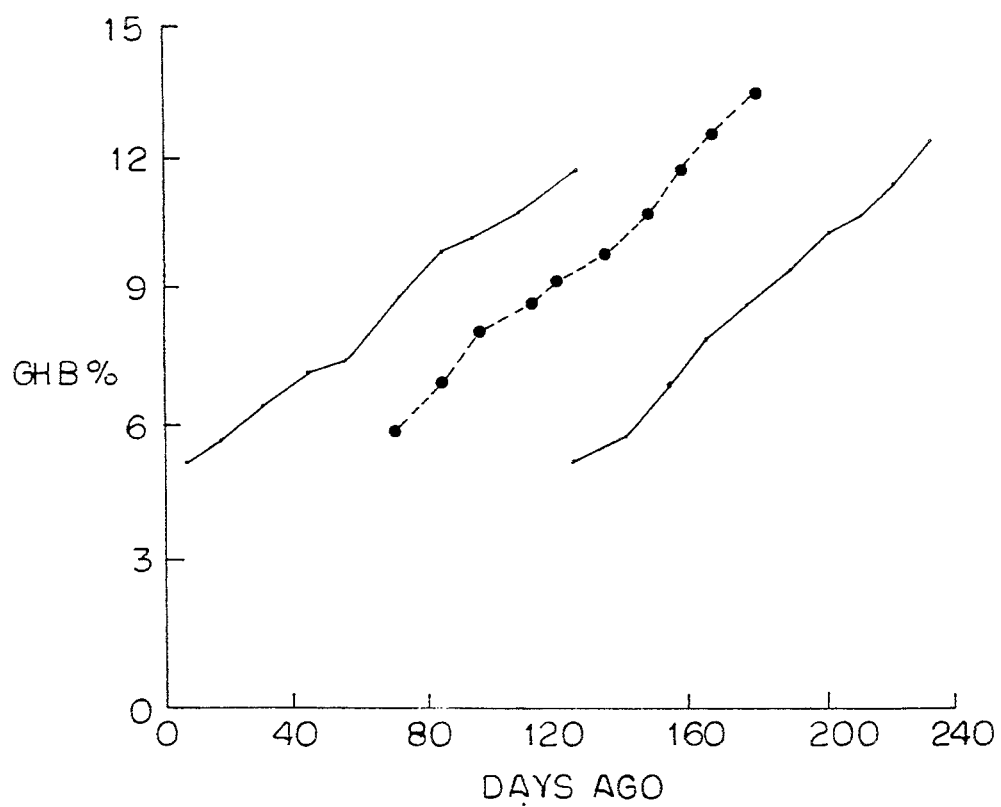
FIG. 4 shows TRG plots derived from three separate blood sample, taken from the same patient at two month intervals.
Figure 5A:
FIG. 5 shows idealized TRG plots to illustrate how clinicians may be misled by untransformed TRG plots. In both 5(a) and 5(b), the solid line represents transformed data and the dashed line, untransformed.
Figure 5B:
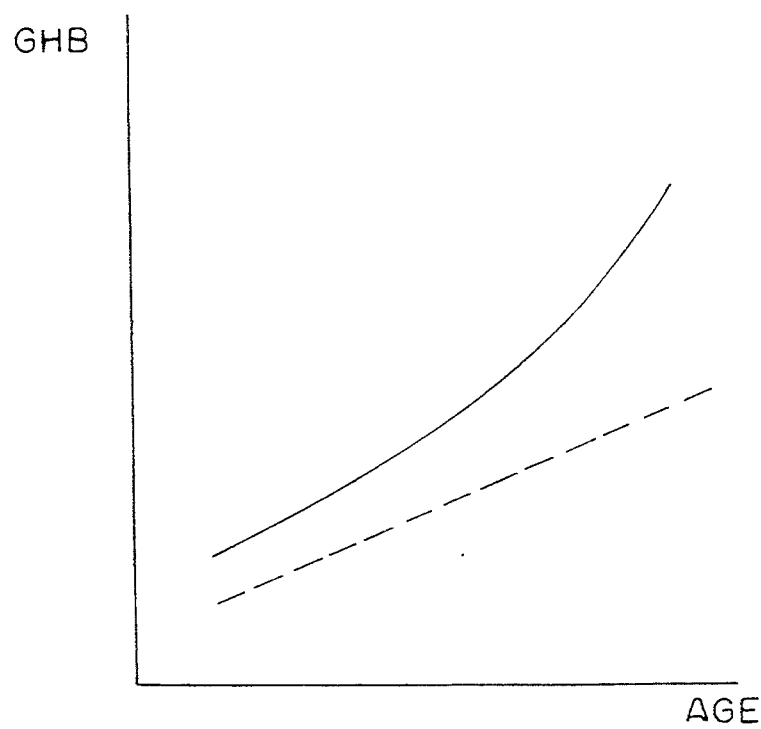

This Example illustrates how a series of samples can be used to obtain a continuing historical record. The three blood samples were taken at approximately two month intervals from one patient. FIG. 4(a) is the untransformed data; FIG. 4(b) shows the effect of the correction for the reversibility of the Amadori rearrangement. After the transform, the samples from three separate dates each have a more or less linear appearance, the three curves are parallel and the discontinuity observed in the younger cells for the middle curve is reproduced in the latest curve (on the left) but in older cells. The latter clearly shows a period of poorer glycemic control at about 60-80 days before the most recent of the three samples. These discontinuities are poorly aligned in the untransformed data.

The middle curve is from a sample taken on Jan. 3, 1990. The lowest two points on the middle curve represent the time period of 25 and 10 days before the sample. Therefore these two points overlap Christmas and New Year of 1989. The patient admitted to some dietary indiscretion during this time. The curve on the left is from a sample taken on Mar. 6, 1990. The point of inflection corresponding to the holiday season appears slightly earlier on this curve because the edges of fractions are not quite lined up according to date. Integrated glycated hemoglobin for the three periods, left to right are 6.6%, 7.5% and 6.9%.

References Cited

Chase H. P., Jackson W. E., Hoops S. L., Cockerham R. S., Archer P. G., O'Brien P. G.: Glucose control and renal and retinal complications of insulin-dependent diabetes. JAMA 261:1155-1160, 1989

Elseweidy M. M., Stallings M, Abraham E. C.: Changes in glycosylated hemoglobin with red cell aging in normal and diabetic subjects and in newborn infants of normal and diabetic mothers. J Lab Clin Med 102:628-636, 1983

Nakishima K, Osamu N, Yukio A, Akira I, Yukio I: Glycated hemoglobin in fractionated erythrocytes. Clin Chem 35:(6)958-962, 1989

American Diabetes Assocn (Position Paper): Blood Glucose Control in Diabetes. Diabetes Care 13:(suppl. 1)16-17, 1990

Saunders A. M.: Method for ascertaining the history of a condition of the body from a single blood sample. U.S. Pat. No. 4,835,097 May 30, 1989

Seaman C, Wyss S, Piomelli S: Decline of energetic metabolism with ageing of erythrocyte and its relationship to cell death. Am J Hematol 8:31-41, 1980

Bunn H. F., Haney D. N., Kamin S, Gabbay K. H., Gallop P. M.: The biosynthesis of human hemoglobin A1c. J Clin Invest 57:1652-1659, 1976

Winocour P. H., Bhatnagar D, Kalsi P, Hillier V. F., Anderson D. C.: Relative usefulness of glycosylated serum albumin and fructosamine during short-term changes in glycemic control in IDDM. Diabetes Care 12(10):665-672, 1989

Piomelli S, Corash L, Davenport D. D., Miraglia J, Amorosi E. L.: In vivo lability of glucose-6-phosphate dehydrogenase in GdA- and Gd (Mediterranean) deficiency. J Clin Invest 47:940-948, 1968.

Leif R. C., Vinograd J: The distribution of buoyant density of human erythrocytes in bovine albumin solutions. Proc N.A.S. 51:520-528, 1964.

Fitzgibbon J. F., Koler R. D., Jones R. T.: Red cell age-related changes of hemogloA1a+b in normal and diabetic subjects. J Clin Invest 58:820-824, 1976.

Saunders, A. M. and Rankin, F JAMA 264:(5)574, 1990

Borun E. R., Figuerora W. G., & Perry S. M.: The distribution of Fe(59) tagged human erthrocytes in centrifuged specimens as a function of cell age. J Clin Invest: 36 676-9 1957.

Abraham E. C., Perry R. E., Stallings M: Application of affinity chromatography for separation and quantitation of glycosylated hemoglobins. J Lab Clin Med 102:187-197, 1983.

Schimke, R. T.: Protein turnover and control of enzyme levels in animal tissues. Accounts of Chemical Research 3:(4)113-120, 1970.

Higgins P. J., Bunn H. F. Kinetic analysis of the nonenzymatic glycosylation of hemoglobin. J Biol Chem 256:5204-5208, 1981.

Mortensen H. B.: Glycated hemoglobin. Reaction and biokinetic studies. Clinical application of hemoglobin A1c in the assessment of metabolic control in children with diabetes mellitus. Danish Med Bull 32:309-328, 1985.

Corash, L: Density-Dependent Red Cell Separation. Clinics in Hematology 14(1):91-107, 1985.

All references in this specification are hereby incorporated by reference to the extent pertinent.

I claim:

1. A method of determining an individual history of blood sugar control which comprises:

(a) taking a sample of red blood cells from the individual, wherein over the life of the red blood cells hemoglobin has been glycosylated to form a glycohemolobin, said reaction being an Amadori rearrangement, which is slowly reversible;

(b) separating the red blood cells according to age into a plurality of cohorts, and determining the average age of the red blood cells in each cohort, the average age differing from cohort-to-cohort;

(c) measuring the average glycohemoglobin levels of said red blood cells on a cohort-by-cohort basis, and correlating said average glycohemoglobin level with said average age for each cohort, while correcting for the reversibility of the Amadori rearrangement, so as to obtain a history of the individual's blood sugar levels over the lifespan of said red blood cells; and (d) examining said history for trends indicative of changes in blood sugar control;

wherein the correction is made by applying a transform of the form $$Y = y \frac{a}{e - bt}$$

where y is the untransformed mean glycohemoglobin level for the cohort, a and b are constants, e is the base of the natural logarithm and t is time.

2. The method of claim 1 wherein the sample is separated into between 8 and 20 age cohorts.

3. The method of claim 1 wherein the mean pyruvate kinase level is determined for each cohort.

4. The method of claim 1 wherein the Amadori rearrangement results in the formation of an adduct of hemoglobin with a sugar selected from the group consisting of fructosamine, 5-deoxy-xylulose-1-phosphate, galactulose and fructose-6-phosphate and the level of said adduct in the sampled red blood cells is determined on a cohort-by-cohort basis.

* * * * *